(12) United States Patent
Farazi et al.

(10) Patent No.: US 10,166,397 B2
(45) Date of Patent: Jan. 1, 2019

(54) SYSTEMS AND METHODS FOR INTERMITTENT MULTIPOINT PACING

(71) Applicant: Pacesetter, Inc., Sunnyvale, CA (US)

(72) Inventors: Taraneh Ghaffari Farazi, San Jose, CA (US); Mark Carlson, Calabasas, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 139 days.

(21) Appl. No.: 15/368,121

(22) Filed: Dec. 2, 2016

(65) Prior Publication Data
US 2017/0157403 A1 Jun. 8, 2017

Related U.S. Application Data

(60) Provisional application No. 62/263,099, filed on Dec. 4, 2015.

(51) Int. Cl.
*A61N 1/368* (2006.01)
*A61N 1/37* (2006.01)
*A61N 1/362* (2006.01)
*A61N 1/365* (2006.01)

(52) U.S. Cl.
CPC ......... *A61N 1/3684* (2013.01); *A61N 1/3627* (2013.01); *A61N 1/3688* (2013.01); *A61N 1/36521* (2013.01); *A61N 1/36564* (2013.01); *A61N 1/36842* (2017.08); *A61N 1/36843* (2017.08); *A61N 1/3708* (2013.01)

(58) Field of Classification Search
CPC .............. A61N 1/3684; A61N 1/36842; A61N 1/36843; A61N 1/3688; A61N 1/3708
See application file for complete search history.

(56) References Cited

U.S. PATENT DOCUMENTS

| | | | |
|---|---|---|---|
| 6,161,041 A | 12/2000 | Stoop et al. | |
| 7,577,479 B2 | 8/2009 | Hartley et al. | |
| 8,224,443 B2 | 7/2012 | KenKnight et al. | |
| 8,428,731 B2 | 4/2013 | Armstrong et al. | |
| 2007/0066998 A1* | 3/2007 | Hansen | A61N 1/056 607/4 |

FOREIGN PATENT DOCUMENTS

WO 01/76691 A1 10/2001

OTHER PUBLICATIONS

Christopher Aldo Rinaldi, et al., "A Review of Multisite Pacing to Achieve Cardiac Resynchronization Therapy," Eurospace, 2015, 17, 7-17.

(Continued)

*Primary Examiner* — William J Levicky
(74) *Attorney, Agent, or Firm* — Theresa A. Raymer

(57) ABSTRACT

The present disclosure provides systems and methods for applying intermittent multipoint pacing. An implantable cardiac device includes a plurality of electrodes, and a controller communicatively coupled to the plurality of electrodes and configured to cause the plurality of electrodes to alternate between applying multipoint pacing (MPP) and standard biventricular pacing (BiV) to a patient's heart.

20 Claims, 5 Drawing Sheets

(56) References Cited

OTHER PUBLICATIONS

Christophe Leclercq, et al., "A Randomized Comparison of Triple-Site Versus Dual-Site Ventricular Stimulation in Patients with Congestive Heart Failure," Journal of American College of Cardiology, vol. 51, No. 15, 2008, pp. 1455-1462.
David D. Spragg, et al., "Optimal Left Ventricular Endocardial Pacing Sites for Cardiac Resynchronization Therapy in Patients with Ischemic Cardiomyopathy." Journal of American College of Cardiology, vol. 56, No. 10, 2010, 8 pages.
Bernard Thibault, et al., "Acute Haemodynamic Comparison of Multisite and Biventricular Pacing with a Quadripolar Left Ventricular Lead." Eurospace, 2013, 15, 984-991.
Antonios P. Antoniadlis, et al., "Multisite Pacing for Cardiac Resynchronization Therapy: Promise Pitfalls," Curr Cardiol Rep, 2016, 18:64.
Danilo Ricciardi, "Non Invasive Hemodynamic Optimization of Cardiac Resynchronization Therapy with Multipoint Left Ventricular Pacing: A Multicenter Pilot Experience," Cardiovascular Sciences Department, Campus Bio-Medico University of Rome.

\* cited by examiner

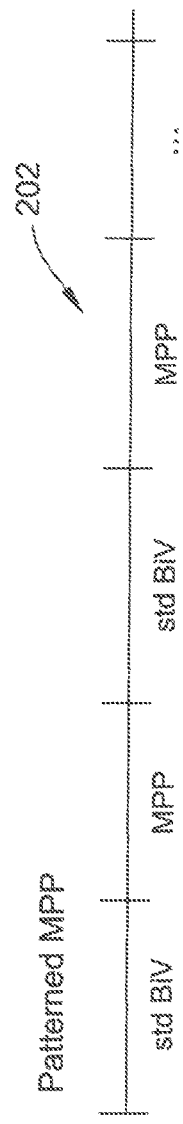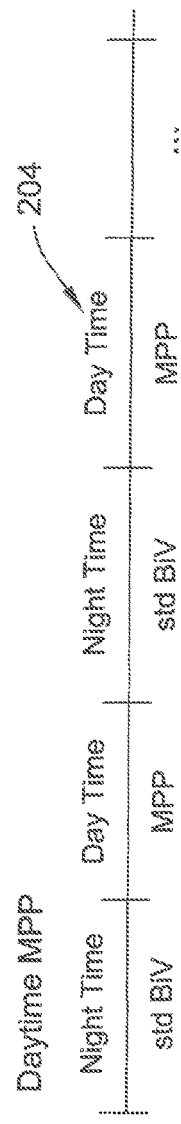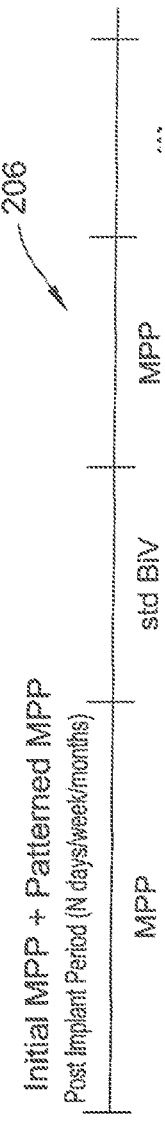

SYSTEMS AND METHODS FOR INTERMITTENT MULTIPOINT PACING

A. PRIORITY

This application claims the benefit of U.S. Provisional Application No. 62/263,099, filed Dec. 4, 2015, which is incorporated here by reference in its entirety to provide continuity of disclosure.

B. FIELD OF THE DISCLOSURE

The present disclosure relates generally to cardiac stimulation systems, and more particularly to an implantable cardiac device that alternates between applying multipoint pacing and standard biventricular pacing.

C. BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become develop leaks, allowing regurgitation or backflow of blood. The impairment of arterial circulation deprives vital organs of oxygen and nutrients. Fatigue, weakness, and inability to carry out daily tasks may result.

Current standard treatment for HF is typically centered around medical treatment using ACE inhibitors, ARBs, diuretics, and beta blockers. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some HF patients are refractory to drug therapy, have a poor prognosis and limited exercise tolerance. In recent years cardiac pacing, in particular cardiac resynchronization therapy (CRT), has emerged as an effective treatment for many patients with drug-refractory HF.

Long-term clinical benefits of CRT are influenced by patient selection, lead placement, and device programming. For example, a variety of intracardiac electrogram (IEGM) based algorithms have been developed to predict which atrioventricular (AV) and interventricular conduction (VV) delays will facilitate maximizing clinical benefits. For a viable myocardium, mechanical contraction is coupled with electrical conduction.

In multipoint pacing (MPP), two left ventricular (LV) pulses are delivered during a single pacing cycle. MPP has been shown to increase LV reverse remodeling, increase LV function acutely, convert non-responders to CRT into responders, and further improve response in those who respond to conventional CRT. Further, use of MPP has been shown to result in increased LV function three to twelve months after therapy, as compared to conventional CRT. Although MPP is beneficial, MPP also generally reduces device longevity, as it requires more power than conventional CRT methods. Accordingly, it would be desirable to realize the benefits of MPP at a reduced power consumption.

BRIEF SUMMARY OF THE DISCLOSURE

In one embodiment, the present disclosure is directed to an implantable cardiac device for providing cardiac resynchronization therapy. The implantable cardiac device includes a plurality of electrodes, and a controller communicatively coupled to the plurality of electrodes and configured to cause the plurality of electrodes to alternate between applying multipoint pacing (MPP) and standard biventricular pacing (BiV) to a patient's heart.

In another embodiment, the present disclosure is directed to a computing device for use in an implantable cardiac device that includes a plurality of electrodes. The computing device includes a memory device, and a processor communicatively coupled to the memory device, the processor configured to cause the plurality of electrodes to alternate between applying multipoint pacing (MPP) and standard biventricular pacing (BiV) to a patient's heart.

In another embodiment, the present disclosure is directed to a method for applying cardiac resynchronization therapy to a patient. The method includes communicatively coupling a plurality of electrodes to a controller, and causing, using the controller, the plurality of electrodes to alternate between applying multipoint pacing (MPP) and standard biventricular pacing (BiV) to a heart of the patient.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 2A-2C are schematic timelines illustrating of example therapy schemes that may be implemented using the implantable stimulation device shown in FIGS. 1A and 1B.

Corresponding reference characters indicate corresponding parts throughout the several views of the drawings.

DETAILED DESCRIPTION OF THE DISCLOSURE

The present disclosure provides systems and methods for applying intermittent multipoint pacing. An implantable cardiac device includes a plurality of electrodes. A controller communicatively coupled to the plurality of electrodes is configured to cause the plurality of electrodes to alternate between applying multipoint pacing (MPP) and standard biventricular pacing (BiV) to a patient's heart.

Figure 1A:
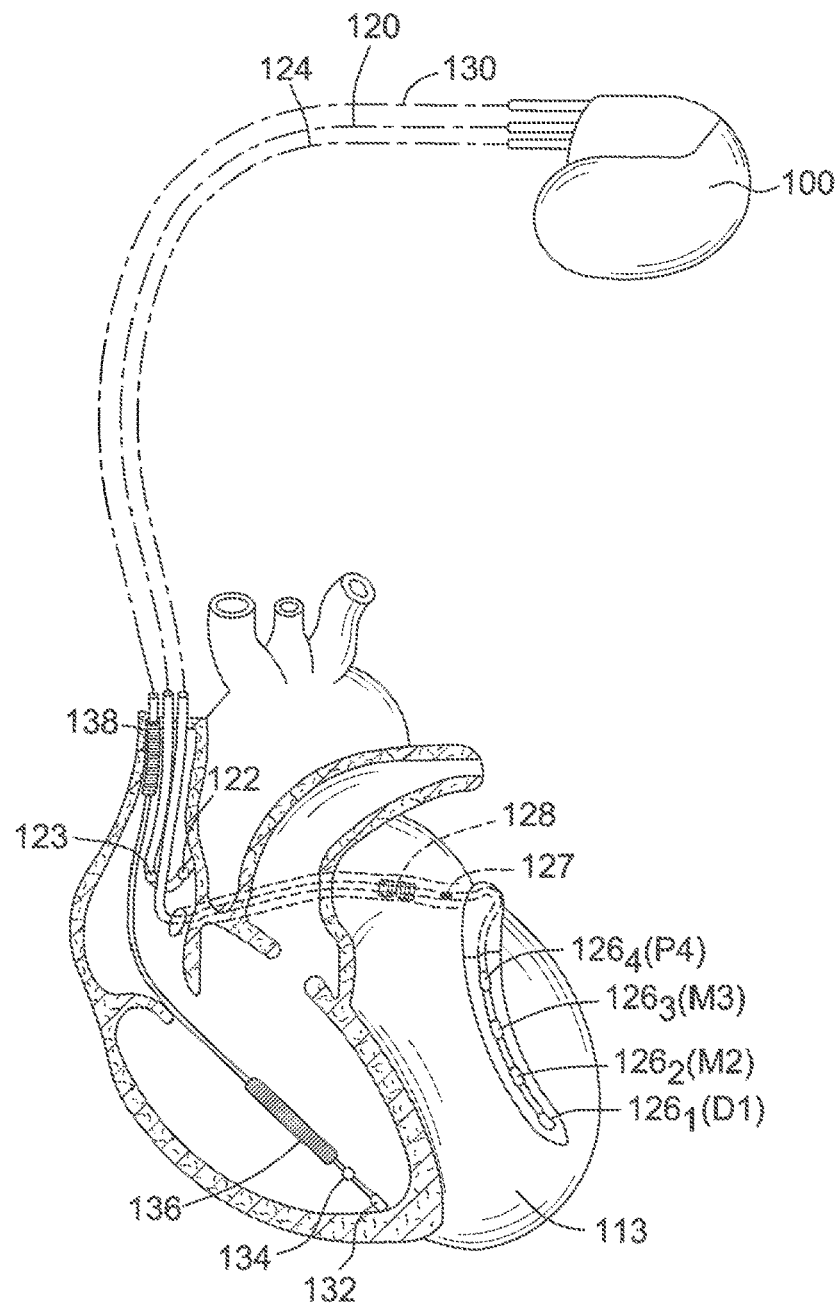
FIG. 1A is a simplified, partly cutaway view illustrating an implantable stimulation device in electrical communication with at least three leads implanted into a patient's heart for delivering multi-chamber stimulation and shock therapy and sensing cardiac activity.
Figure 1B:
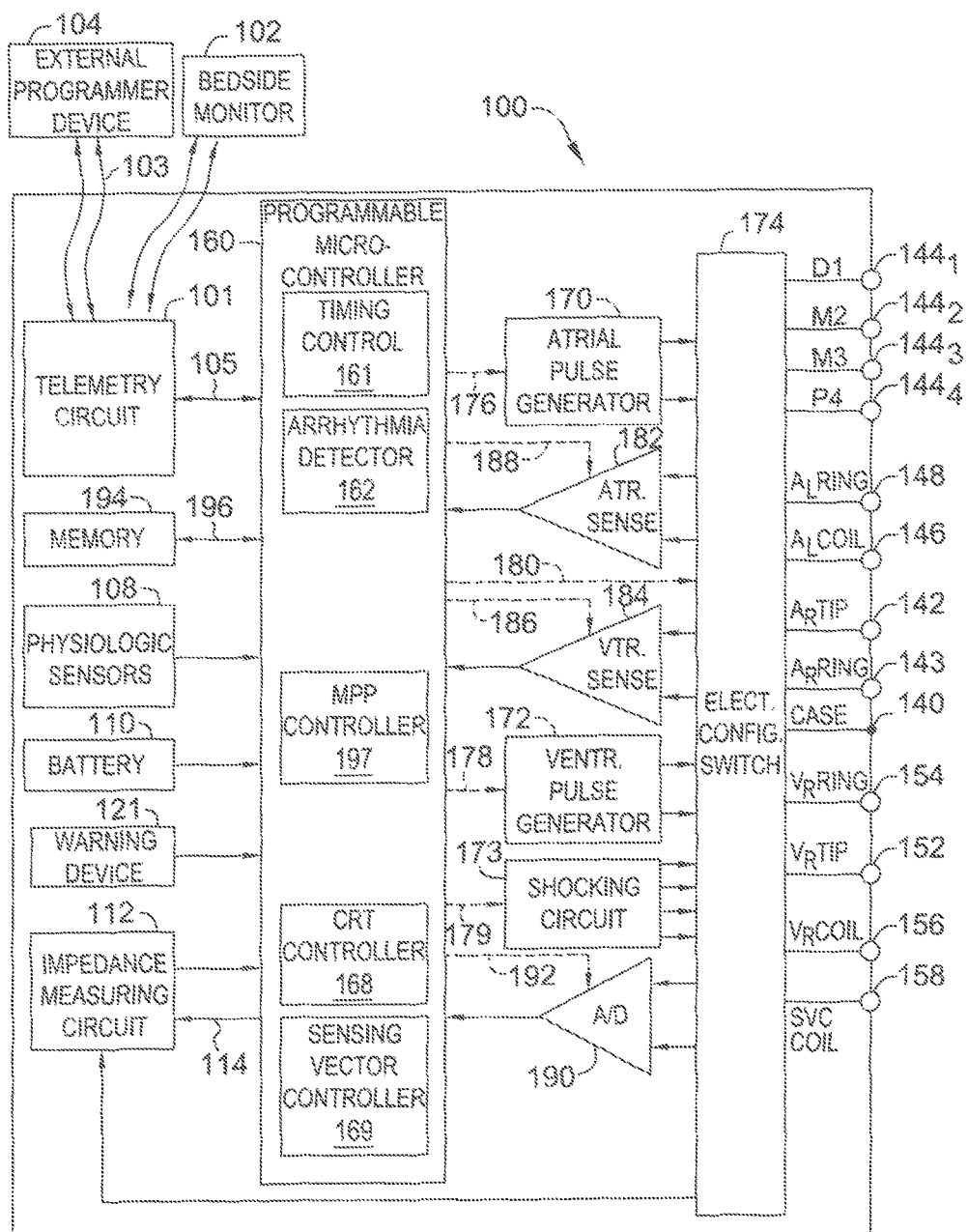
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multipoint pacing (MPP). To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by St. Jude Medical Inc. (headquartered in St. Paul, Minn.), which includes four pacing electrodes on the left ventricular lead—enabling up to ten pacing configurations. In an embodiments, a Quartet™ LV lead is used with a Quadra Assura MP™ RF CRT-D, developed by St. Jude Medical Inc.

LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil electrode 136). Below is a list of exemplary vectors that can be used for pacing and/or sensing using LV electrodes D1, M2, M3 and P4 with and without the RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1 B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1 B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals, 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to RA ring electrode 123. To achieve left chamber sensing, pacing and shocking, the connector includes an LV tip terminal $144_1$ adapted for connection to the D1 electrode and additional LV electrode terminals $144_2$, $144_3$ and $144_4$ terminals adapted for connection to the M2, M3 and P4 electrodes of quadra-pole LV lead 124.

The connector also includes an LA ring terminal ($A_L$ RING) 146 and an LA shocking terminal ($A_L$ COIL) 148, which are adapted for connection to LA ring electrode 127 and the LA coil ($A_L$ COIL) electrode 128, respectively. To support right chamber sensing, pacing and shocking, the connector further includes an RV tip terminal ($V_R$ TIP) 152, an RV ring terminal ($V_R$ RING) 154, an RV shocking terminal ($V_R$ COIL) 156, and an SVC shocking terminal (SVC COIL) 158, which are adapted for connection to RV tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1 B, an atrial pulse generator 170 (controlled by a control signal 176) and a ventricular pulse generator 172 (controlled by a control signal 178) generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc.

Microcontroller 160 further includes an arrhythmia detector 162 that can be utilized by pacemaker/ICD 100 for determining desirable times to administer various therapies. Additional components of the microcontroller may include a cardiac resynchronization therapy (CRT) controller 168 to control CRT and a multipoint pacing (MPP) controller 197 (described in detail below).

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain IEGMs in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, CRT controller 168 and MPP controller 197 may be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar (e.g., using unipolar leads in the atrium and ventricle and performing atrial sensing in a bipolar way using the ventricular lead tip as an indifferent electrode), etc.) by selectively closing the appropriate combination of switches (not shown) as is known in the art. The switch also switches among the various LV electrodes.

Atrial sensing circuits 182 (controlled by a control signal 188) and ventricular sensing circuits 184 (controlled by a control signal 186) may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190 (controlled by a control signal 192). Data acquisition system 190 is configured to acquire intracardiac electrogram signals, convert the raw analog data into a digital signal, and store the digital signals for later processing and/or telemetric transmission to an external programmer device 104 or a bedside monitor 102 or personal advisory module. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external programmer device 104 or bedside monitor 102, such as a programmer, transtelephonic transceiver, or a diagnostic system analyzer. The telemetry circuit 101 is activated by the microcontroller by a control signal 105. Telemetry circuit 101 advantageously allows intracardiac electrograms and status information relating to the operation of pacemaker/ICD 100 (as contained in microcontroller 160 or memory 194) to be sent to external programmer device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 (i.e., using RV coil electrode 136 as a common electrode).

In this embodiment, microcontroller 160 further includes multipoint pacing (MPP) controller 197. MPP controller 197 controls pacemaker/ICD 100 to deliver patterned and/or demand-based MPP, as described herein. In MPP, two left ventricular (LV) pulses are delivered during a single pacing cycle. MPP generally improves contractility and overall cardiac output.

Pacemaker/ICD 100 is provided as an example. One or ordinary skill in the art would understand that embodiments described herein can be used with alternative types of implantable devices. Accordingly, embodiments described herein should not be limited to use only with the above described device.

As described below, pacemaker/ICD 100 is a CRT device with MPP capability that can deliver MPP therapy in regular periods that are separated by periods in which standard biventricular pacing (std BiV) (i.e., pacing in both the left and right ventricle during a cardiac cycle in synchrony with atrial activation but not necessarily simultaneously with atrial activation) is delivered. Accordingly, instead of continuously delivering MPP, pacemaker/ICD 100 delivers MPP intermittently and efficiently to realize the benefits of MPP at a reduced battery usage. Possible therapy schemes may include at least one of the example therapy schemes described below, including combinations of the example therapy schemes.

FIGS. 2A-2C are schematic timelines of example therapy schemes. FIG. 2A is a timeline 202 of an example patterned MPP therapy scheme. As shown in timeline 202, therapy alternates between std BiV and MPP. In this embodiment, MPP is programmed (e.g., via MPP controller 197) to be activated regularly and periodically. For example, MPP may be activated daily, weekly, or monthly for a predetermined period of time (e.g., six hours, two days, one week, etc.). Std BiV is delivered when MPP is not activated.

For example, FIG. 2B is a timeline 204 of a daytime MPP therapy scheme. As shown in timeline 204, MPP is turned on daily (e.g., from 8 AM to 8 PM) and std BiV is delivered when MPP is not activated (e.g., from 8 PM to 8 AM). In another example, MPP may be turned on for one month every other month, such that pacing alternates between MPP and std BiV monthly. Those of skill in the art will appreciate that MPP and std BiV may be alternated using any suitable scheme.

To determine between day and night, the device may use an activity sensor (e.g., an accelerometer) or an activity posture sensor to determine day time versus night time. Further, this would accommodate patients who are actually active at night and asleep during the day. Alternatively the device could use the CPU clock to determine day and night.

In some embodiments, activation of a patterned MPP scheme, such as those shown in FIGS. 2A and 2B, is triggered using a sensor communicatively coupled to MPP controller 197. For example, a patterned MPP scheme may be triggered based on patient activity or cardiac demand. Patient activity may be detected, for example, by a 3D accelerometer. Cardiac demand may be detected, for example, by heart rate as detected by the IEGM and device processor, impedance measured by an impedance sensor, pressure measured by a pressure sensor, cardiac volume measured by a volume sensor, and/or cardiac phenomena observed by an optical sensor.

In another example, heart failure monitoring measurements such as left atrial pressure or pulmonary artery pressure as measured by a CardioMEMS™ HF System (available from St Jude Medical) could be used to automatically determine the use of BiV versus MPP pacing. In this example, MPP ON times (i.e., times when MPP is activated) would be triggered by an increase in left atrial pressure or pulmonary artery pressure above a predetermined threshold. The threshold could either be programmable or automatically set by the device based on patient's normal daily variation in pressure. In another example, activation of MPP could be triggered based on electrical timing between ventricular electrodes. For such schemes, a patterned MPP scheme may be triggered, for example, when a measured parameter (e.g., pressure, impedance, volume, etc.) exceeds a predetermined threshold or falls below a predetermined threshold.

In some embodiments, the MPP therapy scheme is triggered in response to a user input. For example, a patient or physician may initiate a desired MPP therapy scheme by pressing a button on external programmer device 104 and/or beside monitor 102. This may be referred to as a demand-based therapy scheme. The MPP therapy scheme triggered by user input may be any of the above-described therapy schemes, or may be a single session of MPP therapy that is delivered for a predetermined period of time.

Further, in at least some embodiments, an initial session of MPP therapy is delivered prior to entering the above-described therapy schemes. For example, after implantation of pacemaker/ICD 100, the patient may receive MPP for three months continuously, followed by a patterned MPP therapy scheme. Such a configuration is shown in timeline 206 of FIG. 2C.

In another embodiment, a set of alternate MPP settings (e.g., vector combinations and parameters) may be selected and stored (e.g., using external programmer device 104) during initial programming. During a first MPP therapy scheme, if a trigger event (e.g., detection of phrenic nerve stimulation) occurs, pacemaker/ICD 100 automatically switches to the alternate MPP settings.

Battery usage information may also be used to control operation of pacemaker/ICD 100. For example, in one embodiment, battery usage information, MPP settings, and hemodynamic sensor data are used to set limits for an MPP therapy scheme to facilitate achieving a balance between best patient hemodynamics outcomes and longest device longevity. In another embodiment, pacemaker/ICD 100 uses battery usage information and MPP settings to set limits for an MPP therapy scheme to achieve optimal device longevity. For example, pacemaker/ICD 100 may use an algorithm that uses values of the programmed output setting for MPP therapy to determine an MPP therapy interval duration that facilitates optimal battery use while maintaining effective therapy. Specifically, for an optimal battery use, pacemaker/ICD 100 might either limit the maximum output settings (e.g., left ventricular pacing output voltage and pulse width) and/or limit the maximum duration of an MPP ON interval. Additionally, pacemaker/ICD 100 may limit a margin between capture threshold and pacing output. In another embodiment, pacemaker/ICD 100 operates with MPP ON durations as determined above (i.e., that are derived to facilitate achieving optimal battery life) for when the patient is stable. However, when pacemaker/ICD 100 determines the patient to be unstable or trending toward instability from a cardiac function/hemodynamic standpoint (as measured by a variety of sensors (e.g., those discussed above) or as determined by existing device-based HF algorithms that use such sensor measurements), the MPP ON duration may be based on the most optimal setting for providing the most efficacious therapy without regard to battery usage. In the examples above, the determined interval durations may be used as a default setting or an upper limit.

Figure 3:
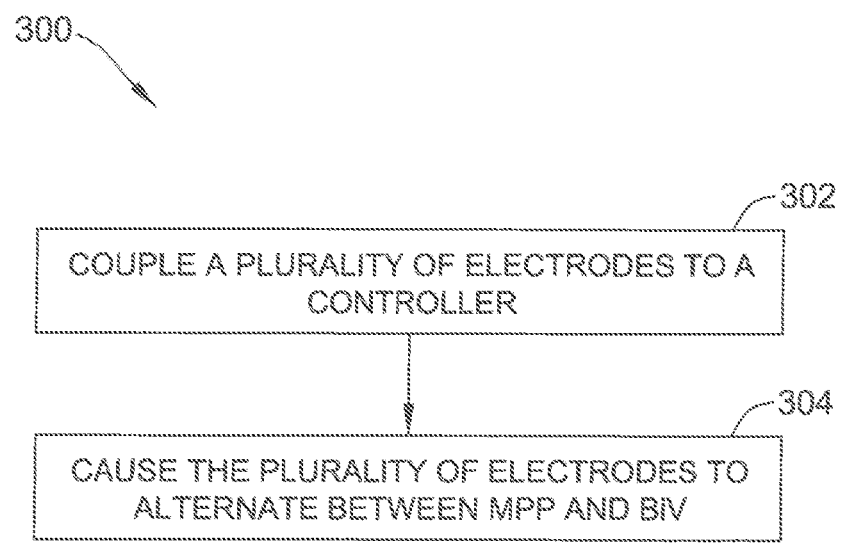
FIG. 3 is a flow diagram of one embodiment of a method for applying cardiac resynchronization therapy to a patient that may be implemented using the implantable stimulation device shown in FIGS. 1A and 1B.

FIG. 3 is a flow diagram of one embodiment of a method 300 for applying cardiac resynchronization therapy to a patient. Method 300 may be implemented, for example, using pacemaker/ICD 100. Method 300 includes communicatively coupling 302 a plurality of electrodes to a controller. Once coupled 302, method 300 includes causing 304, using the controller, the plurality of electrodes to alternate between applying MPP and BiV to a heart of the patient. The alternating between MPP and BiV may be performed, for example, in accordance with one or more of the techniques described above.

Figure 4:
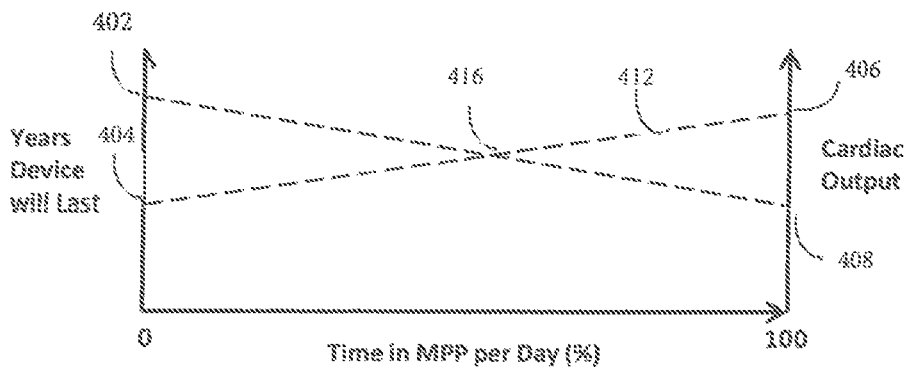
FIG. 4 is a plot illustrating a relationship between percent of time spent in MPP, projected longevity, and hemodynamics.

FIG. 4 is a plot depicting a relationship between percent of time spent in MPP, projected longevity, and hemodynamics. In an embodiment of a method of the current disclosure, pacing thresholds at LV1 and LV2 for MPP, pacing threshold at LV for BiV, and pacing thresholds at RA and RV can be used to calculate projected device longevity for different proportions of the day when MPP is ON. 100% BiV pacing can be assumed since that is the target for CRT therapy. Point 402 depicts the years the implantable cardiac device will last if MPP is used 0% of the time. Point 404 depicts the years the implantable cardiac device will last if MPP is used 100% of the time. In an embodiment, hemodynamic optimization is performed at implant. Cardiac output (CO), ejection fraction (EF), LV dP/dt$_{max}$ (maximum rate of pressure change), stroke work, stroke volume, cardiogenic impedance, time derivative of left ventricular pressure, left atrial pressure, pulmonary artery pressure (PA pressure), heart rate, arterial pulse pressure, or other hemodynamic measure are measured or derived at 0% MPP and 100% MPP. In certain embodiments, a CD Leycom®'s Pressure-Volume (PV) Loop System, available from Millar, is used to assess the patient's hemodynamics at 0% MPP and 100% MPP. In certain embodiments, left atrial pressure or pulmonary artery pressure (PA pressure) as measured by a CardioMEMS™ HF System (available from St Jude Medical) and used to assess the patient's hemodynamics at 0% MPP and 100% MPP. The plot of FIG. 4 assumes a linear relationship between time in MPP and the hemodynamic measurement (e.g., CO) (line 412). Point 406 depicts CO if MPP is used 100% of the time. Point 408 depicts CO if MPP is used 0% of the time.

Figure 5:
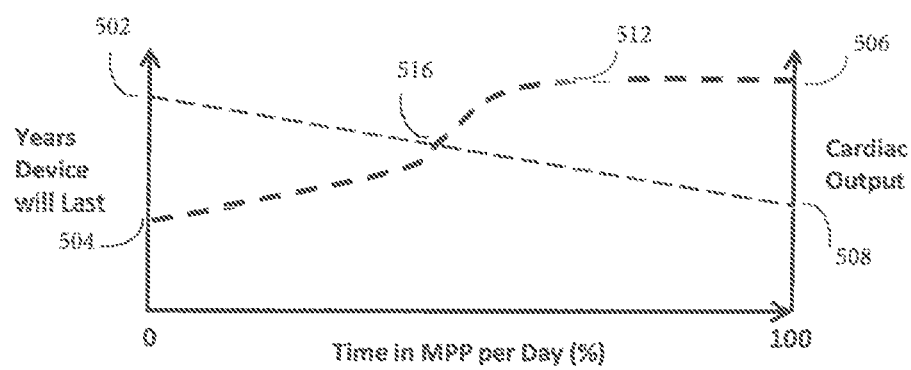
FIG. 5 is a plot illustrating a relationship between percent of time spent in MPP, projected longevity, and hemodynamics.

In an embodiment, illustrated in FIG. 5, an implanted hemodynamic sensor is used to determine the actual relationship, which can be "learned" over a period of time by varying the percent of time spent in MPP from day to day. The hemodynamic measurement, e.g., CO, can be measured and/or derived either once a day or more frequently and then averaged. After the actual relationship between percent of time in MPP and CO is learned, it may look like that shown in FIG. 5 (line 512). Point 502 depicts the years the implantable cardiac device will last if MPP is used 0% of the time. Point 504 depicts the years the implantable cardiac device will last if MPP is used 100% of the time. Point 506 depicts CO if MPP is used 100% of the time. Point 508 depicts CO if MPP is used 0% of the time.

The plots of FIG. 4 or 5 can be presented to the clinician and the clinician can choose where on the plot he/she wants to be and then the device can set the amount of time MPP should be on and amount of time it should be off to achieve it. Alternatively, the place where the two lines cross (416 in FIG. 4, 516 in FIG. 5) or another location on the plot can be automatically chosen by the implantable cardiac device as the target, and pacing parameters may be automatically adjusted accordingly.

In an alternative embodiment, the absolute minimum requirements for longevity and/or the hemodynamic measurement (e.g., CO) are programmed and the implantable cardiac device sets the time spent in MPP to meet that requirement.

In an alternative embodiment, if it is determined that the relationship between time spent in MPP and the hemodynamic measurement is not linear (which is most likely) and there is a plateau (as shown in FIG. 5, line 512), it may be most beneficial to set the time in MPP per day at the point where the hemodynamic measurement plateau begins. In an embodiment, the plateau could be identified by taking a derivative of the CO curve and finding where the derivative comes close to zero within some error.

In an embodiment, the time of day when MPP is turned ON and OFF is varied during the learning period. It may be found that for some patients turning MPP OFF at night will not impact hemodynamics or will have a minimal impact. For example, a similar plot to FIG. 5 may be created where MPP is turned OFF at night. The hours during the night (e.g., 8 hours) may be excluded from the calculation of "time in MPP per Day %" (e.g., the percentage of time in MPP over a 16 hour period of the patient being awake can be used).

The % time in MPP during waking hours can be overlaid on the plot of FIG. 5. If the overlaid plots are sufficiently similar (e.g., the difference is within a threshold amount) or the plot of MPP during waking hours demonstrates an improvement in a hemodynamic measurement over that shown in FIG. 5 (where MPP is not turned OFF at night), MPP may be programmed to turn OFF at night going forward. If, on the other hand, the overlaid plots demonstrate a significant detriment to the hemodynamic measurement, MPP may be programmed not to turn OFF 100% of the time at night going forward.

In addition, the curves shown in FIGS. 4 and 5 may change over time. For example, as patient status changes, MPP may produce a beneficial effect early on after CRT is activated, but later the benefit might become reduced. Therefore, the above profile could be "relearned" periodically and the time in MPP per day may be adjusted accordingly. The longevity curve should also be updated as the device updates its own estimate for projected longevity.

The systems and methods described herein take advantage of the concept that added beneficial effects of MPP therapy may be sustained for a period of time during which std BiV is delivered after MPP is turned off. Accordingly, by alternating pacing therapy between MPP and std BiV, the beneficial effects of MPP may be maintained long term, while overall battery usage is reduced as compared to continuous MPP therapy. The period of time between sessions of MPP therapy may be different from patient to patient. Accordingly, in some embodiments, patients may be tested to determine a sufficient period of time.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable cardiac device for providing cardiac resynchronization therapy, the implantable cardiac device comprising:
   a plurality of electrodes; and
   a controller configured to cause alternating between multipoint pacing (MPP) and standard biventricular (BiV) pacing being applied to a patient's heart using the plurality of electrodes or one or more subsets thereof;
   wherein whenever the MPP is applied to the patient's heart, two left ventricular (LV) pulses are delivered per cardiac cycle; and
   wherein whenever the standard BiV pacing is applied to the patient's heart, only one LV pulse is delivered per cardiac cycle.

2. The implantable cardiac device of claim 1, wherein the controller is configured to cause the alternating between the MPP and the standard BiV pacing being applied based on a user input received at an input device communicatively coupled to the controller.

3. The implantable cardiac device of claim 1, wherein the controller is configured to cause the alternating between the MPP and the standard BiV pacing being applied based on battery usage information of the implantable cardiac device.

4. The implantable cardiac device of claim 1, wherein the controller is configured to:
   cause the alternating between the MPP and the standard BiV pacing being applied in accordance with a first therapy scheme;
   cause the alternating between the MPP and the standard BiV pacing being applied in accordance with a second therapy scheme; and
   switch from the first therapy scheme to the second therapy scheme in response to a trigger event.

5. The implantable cardiac device of claim 4, wherein the trigger event is detection of phrenic nerve stimulation.

6. The implantable cardiac device of claim 1, wherein the controller is configured to:
   calculate an MPP ON interval that facilitates optimizing battery life; and
   cause the MPP to be applied for a duration of the MPP ON interval.

7. The implantable cardiac device of claim 1, further comprising one or more sensors communicatively coupled to the controller, wherein the controller is configured to cause the alternating between the MPP and the standard BiV pacing being applied based on at least one parameter value measured by at least one of the one or more sensors.

8. The implantable cardiac device of claim 7, wherein the one or more sensors comprise at least one of a pressure sensor, an impedance sensor, a volume sensor, a cardiac activity sensor, or an optical sensor.

9. A computing device for use in an implantable cardiac device that includes a plurality of electrodes, the computing device comprising:
   a memory device including program code stored therein; and
   a processor communicatively coupled to the memory device, the processor, by executing the program code stored in the memory device, configured to cause alternating between multipoint pacing (MPP) and standard biventricular (BiV) pacing being applied to a patient's heart using the plurality of electrodes or one or more subsets thereof;
   wherein whenever the MPP is applied to the patient's heart, two left ventricular (LV) pulses are delivered per cardiac cycle; and wherein whenever the standard BiV pacing is applied to the patient's heart, only one LV pulse is delivered per cardiac cycle.

10. The computing device of claim 9, wherein the processor is configured to cause the alternating between the MPP and the standard BiV pacing being applied based on a user input received at an input device communicatively coupled to the processor.

11. The computing device of claim 9, wherein the processor is configured to cause the alternating between the MPP and the standard BiV pacing being applied based on battery usage information of the implantable cardiac device.

12. The computing device of claim 9, wherein the processor is configured to:
cause the alternating between the MPP and the standard BiV pacing being applied in accordance with a first therapy scheme;
cause the alternating between the MPP and the standard BiV pacing being applied in accordance with a second therapy scheme; and
switch from the first therapy scheme to the second therapy scheme in response to a trigger event.

13. The computing device of claim 12, wherein the trigger event is detection of phrenic nerve stimulation.

14. The computing device of claim 9, wherein the processor is configured to:
calculate an MPP ON interval that facilitates optimizing battery life; and
cause the MPP to be applied for a duration of the MPP ON interval.

15. The computing device of claim 9, wherein the processor is configured to cause the alternating between the MPP and the standard BiV pacing being applied based on a parameter value measured by a sensor communicatively coupled to the processor.

16. A method for applying cardiac resynchronization therapy to a patient, the method comprising:
communicatively coupling a plurality of electrodes to a controller; and
causing, using the controller, the plurality of electrodes to alternate between applying multipoint pacing (MPP) and standard biventricular (BiV) pacing to a heart of the patient;
wherein whenever the MPP is applied to the patient's heart, two left ventricular (LV) pulses are delivered per cardiac cycle; and
wherein whenever the standard BiV pacing is applied to the patient's heart, only one LV pulse is delivered per cardiac cycle.

17. The method of claim 16, wherein the causing the plurality of electrodes to alternate between applying the MPP and the standard BiV pacing is based on a user input received at an input device communicatively coupled to the controller.

18. The method of claim 16, wherein the causing the plurality of electrodes to alternate between applying the MPP and the standard BiV pacing is based on battery usage information of an implantable cardiac device that includes the controller.

19. The method of claim 16, wherein the causing the plurality of electrodes to alternate between applying the MPP and the standard BiV pacing comprises:
causing the plurality of electrodes to alternate between applying the MPP and the standard BiV pacing in accordance with a first therapy scheme;
detecting a trigger event; and
in response to the detection, causing the plurality of electrodes to alternate between applying the MPP and the standard BiV pacing in accordance with a second therapy scheme.

20. The method of claim 16, wherein the causing the plurality of electrodes to alternate between applying the MPP and the standard BiV pacing comprises:
calculating an MPP ON interval that facilitates optimizing battery life; and
causing the plurality of electrodes to apply the MPP for a duration of the MPP ON interval.

* * * * *